United States Patent
Clark

(10) Patent No.: US 9,472,186 B1
(45) Date of Patent: Oct. 18, 2016

(54) AUTOMATED TRAINING OF A USER AUDIO PROFILE USING TRANSCRIBED MEDICAL RECORD RECORDINGS

(71) Applicant: NVOQ INCORPORATED, Boulder, CO (US)

(72) Inventor: Michael Clark, Longmont, CO (US)

(73) Assignee: NVOQ INCORPORATED, Boulder, CO (US)

( * ) Notice: Subject to any disclaimer, the term of this patent is extended or adjusted under 35 U.S.C. 154(b) by 0 days.

(21) Appl. No.: 14/600,794

(22) Filed: Jan. 20, 2015

Related U.S. Application Data

(60) Provisional application No. 61/932,708, filed on Jan. 28, 2014.

(51) Int. Cl.
*G10L 15/00* (2013.01)
*G10L 15/06* (2013.01)
*G10L 15/26* (2006.01)

(52) U.S. Cl.
CPC .............. *G10L 15/063* (2013.01); *G10L 15/26* (2013.01)

(58) Field of Classification Search
USPC .................................. 704/231–257, 270–275
See application file for complete search history.

(56) References Cited

U.S. PATENT DOCUMENTS

| | | | | |
|---|---|---|---|---|
| 4,839,831 A * | 6/1989 | Imajo | ..................... | F01M 11/10 123/196 S |
| 5,835,893 A * | 11/1998 | Ushioda | ................... | G10L 15/18 704/10 |
| 6,442,519 B1 * | 8/2002 | Kanevsky | ............... | G10L 15/07 704/243 |
| 6,574,597 B1 * | 6/2003 | Mohri | ................... | G10L 15/183 704/251 |
| 7,031,917 B2 * | 4/2006 | Asano | ..................... | G10L 15/20 704/231 |
| 8,423,361 B1 * | 4/2013 | Chang | ..................... | G10L 15/34 704/235 |
| 2004/0088162 A1 * | 5/2004 | He | ........................ | G10L 15/063 704/235 |
| 2013/0096918 A1 * | 4/2013 | Harada | ................... | G10L 15/19 704/251 |

* cited by examiner

*Primary Examiner* — Jesse Pullias
(74) *Attorney, Agent, or Firm* — Perkins Coie LLP

(57) ABSTRACT

An automated system to build a user audio profile for a natural or continuous language speech to text dictation/transcription system is provided. The system uses previously recorded audio files that may have been already transcribed. The previously recorded audio file is split into a plurality of smaller audio files of about 15 seconds in length. The plurality of smaller audio files are matched to the transcribed text (e.g., small text files) or the smaller audio files are transcribed. All, some, or a selection of the small audio files and the small text files are linked as a training pair. The training pair may be edited in certain embodiments herein, both the text and the audio. The training pairs are submitted to the server to build the initial user audio profile.

19 Claims, 5 Drawing Sheets

AUTOMATED TRAINING OF A USER AUDIO PROFILE USING TRANSCRIBED MEDICAL RECORD RECORDINGS

CROSS-REFERENCE TO RELATED PATENT APPLICATIONS

The present application claims priority to U.S. Provisional Patent Application Ser. No. 61/932,708, filed on Jan. 28, 2014, a copy of which is incorporated herein by reference as if set out in full.

FIELD OF THE TECHNOLOGY

The technology of the present application relates generally to speech recognition systems, and more particularly, to apparatuses and methods to allow for the use of pre-recorded and correlated dictated audio and transcribed text files to train a user audio profile in a natural language or continuous speech recognition system.

BACKGROUND

The primary means for communication between people is speech. Since the early 1980s, significant progress has been made to allow people to interface with machines using speech through interfaces such as speech to text engines and text to speech engines. The former converts speech to a machine (and user) readable format; the later converts machine readable code to audio signals for people to hear.

Early speech to text engines operated on a theory of pattern matching. Generally, these machines would record utterances spoken by a person, convert them into phoneme sequences and match these sequences to known words or phrases. For example, the audio of "cat" might produce the phoneme sequence "k ae t", which matches the standard pronunciation of the word "cat". Thus, the pattern matching speech recognition machine converts the audio to a machine readable version "cat." Similarly, a text to speech engine would read the word "cat", convert it into a sequence of phonemes, each of which have a known audio signal, and, when concatenated (and appropriately shaped) produce the sound of "cat" (phonetically: "k ae t"). Pattern matching machines, however, are not significantly robust. Generally, pattern matching machines either operate with a high number of recognizable utterances for a limited variation of voice or operate with a broader variation of voice but a more limited number of recognizable utterances.

More recently, speech recognition engines have moved to continuous or natural language speech recognition (sometimes generically referred to as the processor for convenience). The focus of natural language systems is to match the utterance to a likely vocabulary and phraseology and determine how likely the sequence of language symbols would appear in speech. Generally, a natural language speech recognizer converts audio (or speech) to text in a series of processing steps. First, the audio stream is segmented into frames, which consist of short time-slices of the audio stream. Second, each frame is matched to one or more possible phonemes, or sounds as discussed above. The processor selects the best phoneme, which generally correlates to the strongest match. The processor translates the selected phonemes into words in the third step. The processor next determines the sentence, or sequence of words, that best matches the translated words using a language model. Finally, the sentence, or sequence of words, is normalized into a visually acceptable format of text. For example, a sequence of words that includes "nineteen dollars and thirty six cents" would be normalized to "$19.36".

Determining the likelihood of a particular sequence of language symbols or words is generally called a language model, which is used as outlined briefly above. The language model provides a powerful statistical model to direct a word search based on predecessor words for a span of "n" words. Thus, the language model will use probability and statistically more likely words for similar utterances. For example, the words "see" and "sea" are pronounced substantially the same in the United States of America. Using a language model, the speech recognition engine would populate the phrase: "Ships sail on the sea" correctly because the probability indicates the word sea is more likely to follow the earlier words "ship" and "sail" in the sentence. The mathematics behind the natural language speech recognition system are conventionally known as a hidden Markov model. The hidden Markov model is a system that predicts the next state based on the previous states in the system and the limited number of choices available. The details of the hidden Markov model are reasonably well known in the industry of speech recognition and will not be further described herein.

Speech recognition engines using natural language may have users register with an account. More often than not, the user's device downloads the recognition application, database, and user audio profile to the local device making it a fat or thick client. A user audio profile supplies speaker-dependent parameters required to convert the audio signal of the user's voice into a sequence of phonemes, which are subsequently converted into a sequence of words using the combination of a phonetic dictionary (words spelled out in their phonetic representations) and a language model (expected phraseology). In some instances, the user has a thin client device where the audio is recorded (or received if not necessarily recorded) on the client and routed to a server. The server has the recognition application, database, and user audio profile that allows speech recognition to occur. The client account provides a user audio profile and language model. The audio profile is tuned to the user's voice, vocabulary, and language. The language model provides data regarding the sequence of known words in the corpus, which corpus may be generated from conversational English, medical specialties, accounting, legal, or the like. The initial training of a natural language speech recognition engine generally digitally records the audio signal of a user dictating a number of "known" words and phrases to tune the user audio profile. The known words and phrases are designed to capture the possible range of phonemes present in the user's speech. A statistical model that maps the user's speech audio signal to phonemes is modified to match the user's specific dialect, accent, or the like. These statistical model modifications are stored in a user audio profile for future recall and use. Subsequent training of the speech recognition engine may be individualized by corrections entered by a user to transcripts when the transcribed speech is incorrect.

As can be appreciated, setting up a natural language speech recognition engine requires individualizing the processor to the specific speaker. The user audio profile improves the accuracy of speech recognition as it optimizes the system for a user's specific dialect, pronunciations, or the like. However, the user audio profile training process can be tedious, time consuming, and cumbersome for the user. This is especially true in a technical service profession, such as, for example, healthcare services, financial services, legal services, and the like. The user audio profile for the technical service professions may require more extensive training due to the many technical terms associated with the profession that may not be common in the conventional language of the user. In part due to the initial time commitment, some service providers may elect not to use a speech recognition system as the initial time commitment is not recovered quickly enough to justify the initial time commitment when less efficient alternatives are immediately available. For example, healthcare service providers (e.g., doctors) can dictate medical notes to a recording that may be subsequently transcribed. Many of the dictated medical notes are over telephone based systems where the microphone in the telephone handset is used to record the audio, the speaker in the telephone handset is used to replay the audio, and the touch pad is used to control features of the recording. Other mechanisms for capturing dictated audio are a desktop computer, a workstation, a laptop computer, a tablet, a smartphone, a cellular telephone, a portable audio recorder, a personal digital assistant, or the like, to name but a few exemplary devices. The recording of the dictated medical notes is transcribed into the medical file by a trained technician (e.g., a live person) and returned to the provider for correction, if any.

Thus, against this background, it is desirable to develop improved apparatuses and methods to initially train a user audio profile for a user of a natural language speech recognition system to reduce or eliminate the need for the user to invest an initial time commitment to use the natural language speech recognition system.

SUMMARY

This Summary is provided to introduce a selection of concepts in a simplified form that are further described below in the Detailed Description. This Summary, and the foregoing Background, is not intended to identify key aspects or essential aspects of the claimed subject matter. Moreover, this Summary is not intended for use as an aid in determining the scope of the claimed subject matter.

In one aspect, the technology of the present application builds a user audio profile for a natural or continuous language speech to text dictation/transcription system without having a user commit the initial time investment to train the user audio profile. The technology uses previously recorded audio files that may have been already transcribed or can be transcribed. The previously recorded audio file (e.g. a big audio file generally having minutes of recorded audio) is split into a plurality of smaller audio files of about 15 seconds in length (e.g. a little audio files created from the big audio file). The plurality of smaller audio files are matched to the transcribed text (e.g., small text files) or the smaller audio files are transcribed. In other words, the transcribed file of the entire audio file (e.g. a big transcribed file or a big text file) can be broken into a number of small text files (e.g. a little transcribed file or a little text file) where the text matches the audio of one of the little audio files. All, one, some, or a selection of the small audio files and the small text files are linked as a training pair. The training pair may be edited in certain embodiments herein, both the text and the audio. The training pairs are submitted to the server to build the initial user audio profile without the user actively participating in the initial training of the user audio profile.

These and other aspects of the present system and method will be apparent after consideration of the Detailed Description and Figures herein.

DRAWINGS

Non-limiting and non-exhaustive embodiments of the present invention, including the preferred embodiment, are described with reference to the following figures, wherein like reference numerals refer to like parts throughout the various views unless otherwise specified.

DETAILED DESCRIPTION

The technology of the present application is described more fully below with reference to the accompanying figures, which form a part hereof and show, by way of illustration, specific exemplary embodiments of the technology of the present application. These embodiments are disclosed in sufficient detail to enable those skilled in the art to practice the technology disclosed herein. However, embodiments may be implemented in many different forms and should not be construed as being limited to the embodiments set forth herein. In particular, the technology is described with specific reference to healthcare services, but one of ordinary skill in the art on reading the disclosure will now understand that the technology may be used in other instances including by non-limiting example, legal services and financial services to name but two. The following detailed description is, therefore, not to be taken in a limiting sense. Moreover, the technology of the present application will be described with relation to exemplary embodiments. The word "exemplary" is used herein to mean "serving as an example, instance, or illustration." Any embodiment described herein as "exemplary" is not necessarily to be construed as preferred or advantageous over other embodiments. Additionally, unless specifically identified otherwise, all embodiments described herein should be considered exemplary.

Figure 1:
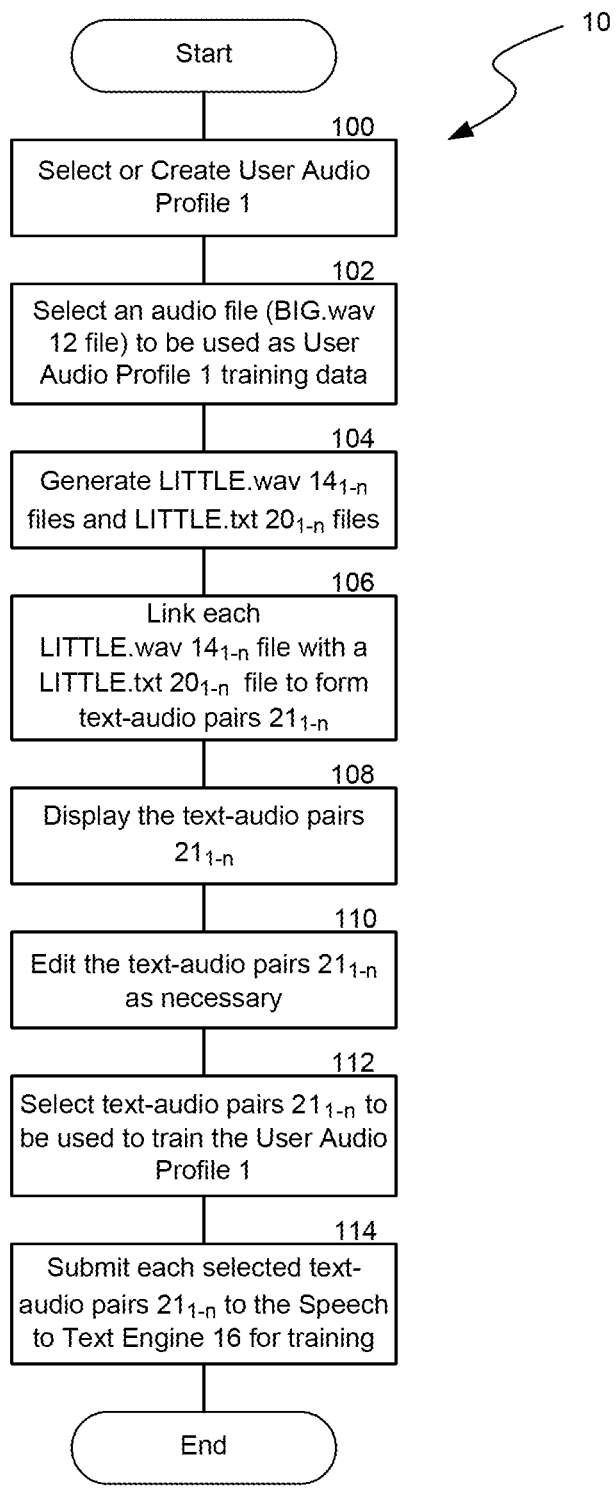
FIG. 1 depicts a flowchart illustrative of a methodology consistent with the technology of the present application.

With reference now to FIG. 1, a flowchart 10 illustrative of a methodology for training a user audio profile consistent with the technology of the present application is provided. While the flowchart 10 illustrates the methodology of a particular exemplary embodiment, one of ordinary skill in the art will now recognize on reading the disclosure that the flowchart is provided in discrete steps for convenience. Many of the discrete steps may be combined into a single step or many of the discrete steps may be separated into multiple steps. Also, while shown in a particular order, the discrete steps of the flowcharts provided herein may be performed in the order shown, another order, or substantially simultaneously.

To initiate the training of a user audio profile, the administrator selects or creates a user audio profile 1, step 100. The user audio profile 1 should be unique to the user and the language model. As an example, the user audio profile may be for Dr. John Doe. Moreover, the user audio profile 1 selected or created also should be identified with a language model to differentiate between possible accounts. For example, Dr. John Doe may have a medical account as well as a personal account. The medical account may be designated john_doe.med while the personal account may be designated john_doe.ord (where ord stands for ordinary). Notice the user audio profile names may follow any convention to establish individual unique identifiers for the user audio profile 1 associated with a particular account. Next, an audio file is selected for processing, step 102. The audio file will generally be indicated as BIG.wav 12 (or big audio file) to signify that this is a large pre-recorded audio file from the user of the user audio profile 1, e.g., john_doe.med. The BIG.wav 12 file typically is a large file comprising, in many cases, several minutes of audio. Generally, the BIG.wav 12 file may comprise anywhere from 2 or 3 minutes of recorded audio to 30 minutes of recorded audio, or in some cases even more. The BIG.wav 12 file generally is overlarge to train the user audio profile, so the BIG.wav 12 must be split into a plurality of LITTLE.wav $14_{1-n}$ files (or little audio file) to be useful as training data, step 104. The BIG.wav 12 file may be split into the plurality of LITTLE.wav $14_{1-n}$ files by manually splitting the files into 10 to 15 second chunks of audio, which may be up to about 15 words. Thus, in the normal course, the BIG.wav 12 file (or big audio file) is at least a minimum of greater than about 15 seconds of recorded audio. Also, a plurality of LITTLE.txt $20_{1-n}$ files must be generated or linked such that each of the plurality of LITTLE.wav $14_{1-n}$ files has a corresponding LITTLE.txt $20_{1-n}$ file, step 106. A concatenation of the LITTLE.txt $20_{1-n}$ files generally corresponds to a BIG.txt file that would be the transcription of the BIG.wav 12 file. The LITTLE.txt $20_{1-n}$ files can be generated from the LITTLE.wav $14_{1-n}$ files or from a BIG.txt file assuming the transcript of the BIG.txt file is tagged, indexed, or the like to correlate to the LITTLE.wav $14_{1-n}$ files.

Figure 2:
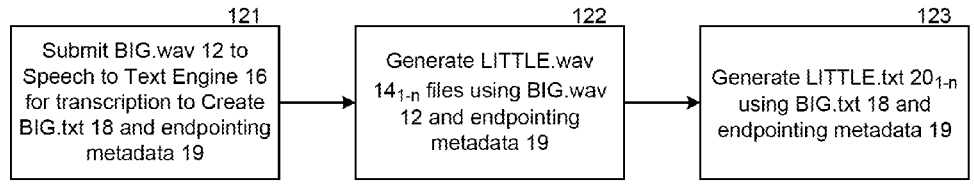
FIG. 2 depicts additional detail of the flowchart of FIG. 1 in one aspect of the technology of the present application.
Figure 3:
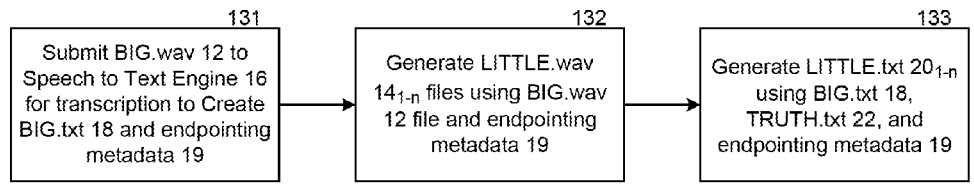
FIG. 3 depicts another detail of the flowchart of FIG. 1 in another aspect of the technology of the present application.
Figure 4:
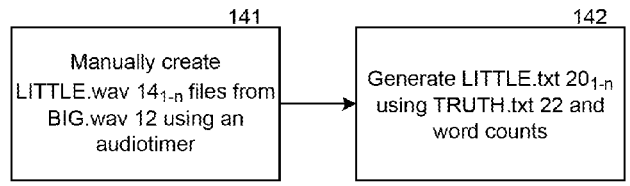
FIG. 4 depicts yet another detail of the flowchart of FIG. 1 in yet another aspect of the technology of the present application.

With reference to FIGS. 2-4, methodologies for generating the plurality of LITTLE.wav $14_{1-n}$ files and the corresponding LITTLE.txt $20_{1-n}$ files are illustrated. The method of FIG. 2 automatically creates LITTLE.wav $14_{1-n}$ files and LITTLE.txt $20_{1-n}$ files using the speech to text engine 16. The plurality of LITTLE.wav $14_{1-n}$ files may be generated automatically by submitting the BIG.wav 12 file to a speech to text engine 16 which will generate endpointing metadata 19 in the process of attempting to transcribe the BIG.wav 12 file (generally, using the default profile as a user-specific voice profile has not been generated) into the BIG.txt 18 file, step 121. The apparatus may use the endpointing metadata 19 to split the BIG.wav 12 file into the plurality of LITTLE.wav $14_{1-n}$ files, step 122. The apparatus may use the endpointing metadata 19 to ensure that each of the plurality of the LITTLE.wav $14_{1-n}$ files terminate (and hence originate) with a complete word or utterance. By splitting BIG.wav 12 after a complete word or utterance, each of LITTLE.WAV $14_{1-n}$ necessarily begins with a new word or utterance. The apparatus may use the transcription (BIG.txt 18) along with the endpointing metadata 19, to generate the plurality of LITTLE.txt $20_{1-n}$ files, step 123.

With reference to FIG. 3, another method of generating LITTLE.wav $14_{1-n}$ and LITTLE.txt $20_{1-n}$ is provided. The method of FIG. 3 automatically generates the LITTLE.wav $14_{1-n}$ files and heuristically maps the LITTLE.txt $20_{1-n}$ files using BIG.txt 18 file, true.txt 22 file, and endpointing metadata 19. Similar to the above, at step 131, BIG.wav 12 is provided to the speech to text engine 16 which produces BIG.txt 18 and endpointing metadata 19 similar to the above. The apparatus may use the endpointing metadata 19 to split BIG.wav 12 into the plurality of LITTLE.wav $14_{1-n}$ files, step 132. Finally, the LITTLE.txt $20_{1-n}$ files are created using TRUTH.txt 22 file, BIG.txt 18 file, and endpointing metadata 19, step 133. TRUTH.txt 21 file is the true text of the BIG.txt 18 file, which is normalized.

With reference to FIG. 4, a manual method of generating the plurality of LITTLE.wav $14_{1-n}$ files and the plurality of LITTLE.txt $20_{1-n}$ files is provided. In this case, the BIG.wav 12 file is manually created using an audio timer to slice the BIG.wav 12 files into the plurality of LITTLE.wav $14_{1-n}$ files, step 141. Similarly, LITTLE.txt $20_{1-n}$ file is manually created by slicing the BIG.txt 18 file using a fixed word count, step 142.

With reference to FIG. 1, each of the plurality of LITTLE.wav $14_{1-n}$ files is matched (or linked by, for example, indexing or tagging) with the transcribed text LITTLE.txt $20_{1-n}$ associated with the audio contained in each of the LITTLE.wav $14_{1-n}$ files, step 106. Each of the LITTLE.wav $14_{1-n}$ files and the corresponding LITTLE.txt $20_{1-n}$ files may be referred to as text-audio pairs $21_{1-n}$ or a training pair. The text associated with the BIG.wav 12 and the plurality of LITTLE.wav $14_{1-n}$ files may be visualized as a BIG.txt 18 file and a corresponding plurality of LITTLE.txt $20_{1-n}$ files. Notice, the plurality of LITTLE.wav $14_{1-n}$ files matches or equals the plurality of LITTLE.txt $20_{1-n}$ files by design. Also, BIG.txt 18 would comprise the plurality of LITTLE.txt $20_{1-n}$ files concatenated. As mentioned above, the BIG.wav 12 file is generally a pre-recorded file of dictation from the user associated with user audio profile 1 with a corresponding transcription, e.g. BIG.txt 18 file. When manually generated, the BIG.txt 18 file is split into a plurality of LITTLE.txt $20_{1-n}$ files by matching the audio and the text. The text file may be annotated or tagged to signify beginning and ending of the text files and words. In one exemplary embodiment, the audio and text is correlated using endpointing metadata 19 identified with speech and time indices on the recording. As can be appreciated, the BIG.txt 18 file may be normalized or formatted text (as described above). To generate the LITTLE.txt $20_{1-n}$ files to match the LITTLE.wav $14_{1-n}$ files, either the BIG.txt 18 or each of the plurality of LITTLE.txt $20_{1-n}$ files must be converted to true text. In the example provided above, the text file must be converted from "$19.36" to "nineteen dollars and thirty six cents" for training purposes. The matched LITTLE.wav $14_{1-n}$ and LITTLE.txt $20_{1-n}$ files are displayed on a graphical user interface as explained in an exemplary embodiment below, step 108.

Figure 5:
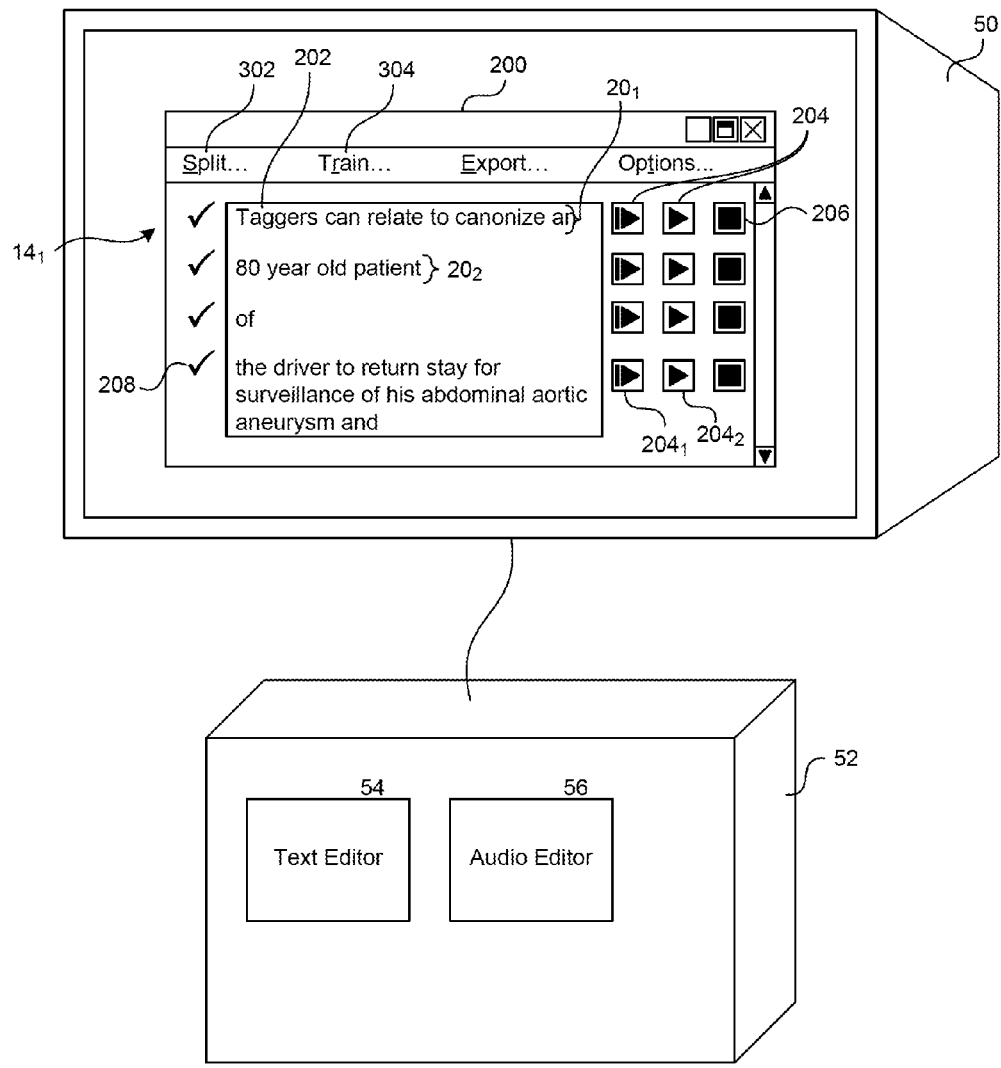
FIG. 5 depicts an exemplary graphical user interface and device incorporating technology consistent with the present application.

With reference to FIG. 5, a representation of the plurality of LITTLE.wav $14_{1-n}$ and the corresponding plurality of LITTLE.txt $20_{1-n}$ files is provided in a graphical user interface ("GUI") 200. The GUI 200 may be displayed on a monitor 50 associated with a processor 52. The processor 52 may be local or remote. The monitor 50, with the GUI 200, and processor 52 may be any number of devices including, for example, a desktop computer, a workstation, a server, a laptop computer, a tablet, a smartphone, a cellular telephone, a personal digital assistant, or the like to name but a few exemplary devices. As can be appreciated, n=4 in the exemplary case shown. The GUI 200 provides a display field 202 to display the text of each LITTLE.txt $20_{1-n}$ file that is associated with each LITTLE.wav $14_{1-n}$ file. The GUI 200 also provides a play button 204 that will play the one of LITTLE.wav $14_{1-n}$ files which is associated with the text in the display 202. The play icon 204 may include a play from beginning icon $204_1$ or a resume play icon $204_2$. The GUI 200 also provides a stop or pause icon 206. More, less, or simply different control icons are possible.

The processor 52 associated with the workstation (whether local or remote) provides a text editor 54 that functions with the GUI 200. Thus, while the audio file LITTLE.wav 14$_1$, for example, is played, an operator at the workstation allows for correction of LITTLE.txt 20$_1$. Also, as can be appreciated, LITTLE.txt 20$_2$ has been shown displayed with normalized text. Thus, the text editor would allow correction of the "80 year old patient" from the normalized text to the raw or true text of "eighty year old patient" as required to allow for user audio profile training Notice, the corrections should be made in the form of true text or raw text rather than normalized text. Alternatively, the processor may convert normalized text to true text or raw text prior to submission of the audio-text pair for training. The processor associated with the workstation also may provide an audio editor 56, such as, for example, a MP3 editor as is available for use with the appropriate operating system, such as, for example, Microsoft, Apple, Linux, or the like. Thus, once the plurality of LITTLE.wav 14$_{1-n}$ files are matched to the LITTLE.txt 20$_{1-n}$ files, the next step comprises correcting (or editing) the text or the audio using the text and/or audio editor, step 110.

The GUI 200 also comprises a select-for-training-field 208 for each pair of each of LITTLE.wav 14$_{1-n}$ and LITTLE.txt 20$_{1-n}$ files (generically referred to as a training pair). The training pair may be selected such that the audio and text is provided to the profile training module, which training modules are generally understood in the art and will not be further explained herein, step 112. The select-for-training-field 208 allows for unacceptable training pairs to be excluded from the training submission.

Figure 6:
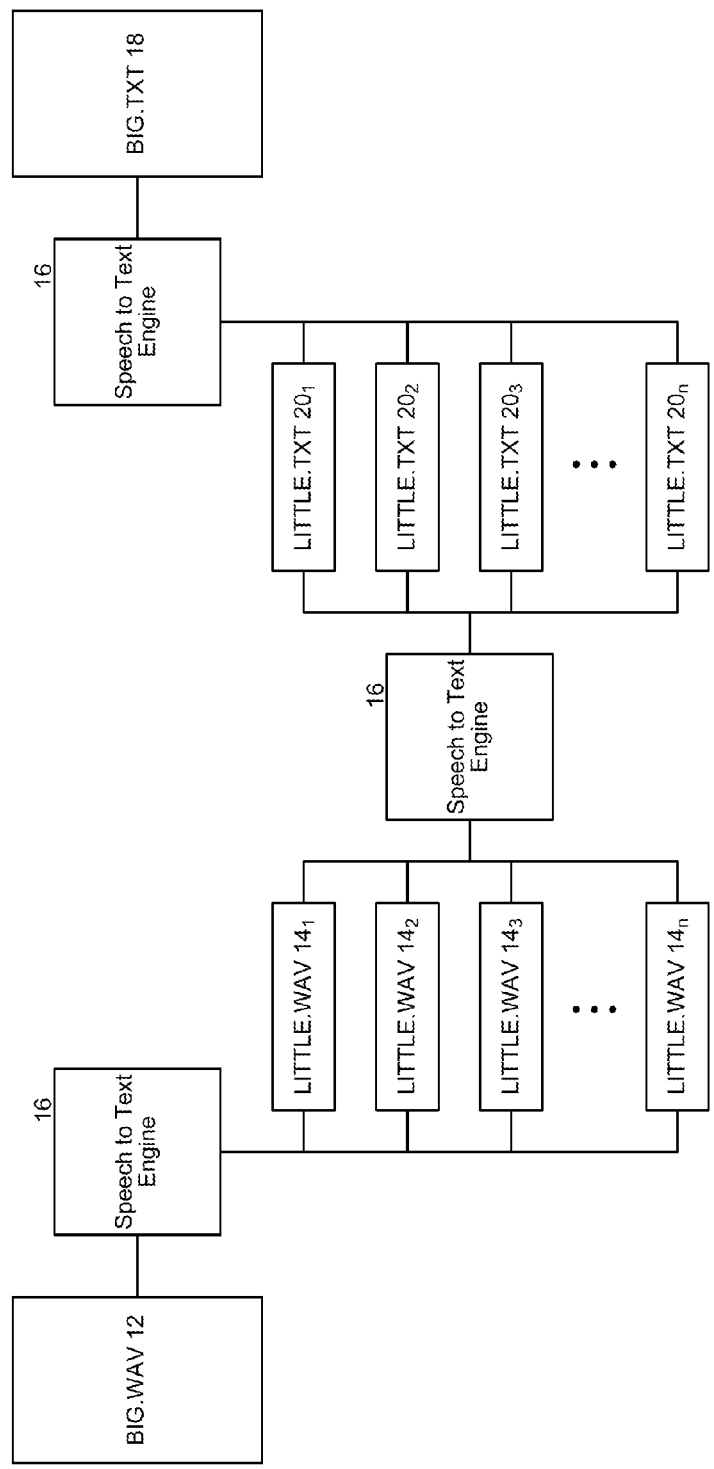
FIG. 6 depicts a functional block diagram of operations consistent with the technology of the present application.

Individual or a group of training pairs are subsequently submitted to the server to build the profile, step 114. With reference to GUI 200, the operation generally described above may be conducted as follows. First, a BIG.wav 12 file is selected. The operator would activate the "split" function by clicking the split button 302. The split function would generate the plurality of LITTLE.wav 14$_{1-n}$ files using a speech to text engine 16 as shown in FIG. 6. The split function also may generate the LITTLE.txt files 20$_{1-n}$ using the speech to text engine 16 as shown in FIG. 6 also. Conversely, the LITTLE.txt files 20$_{1-n}$ could be matched by word and time indices. The speech to text engine 16 could generate the BIG.txt file 18 by combining the LITTLE.txt files 20$_{1-n}$ as required. Once GUI 200 is populated with the training pairs (in other words, the paired training audio file and the training text file), the operator selects the "train" icon 304 to transmit the training pair(s) to the server to build the user audio profile. Thus, while the user associated with the user audio profile under training produces the original audio file (BIG.wav 12) and perhaps corrects a transcription file (BIG.txt), the user does not actively participate in the initial training of the user audio profile but nonetheless does train the profile.

Figure 7:
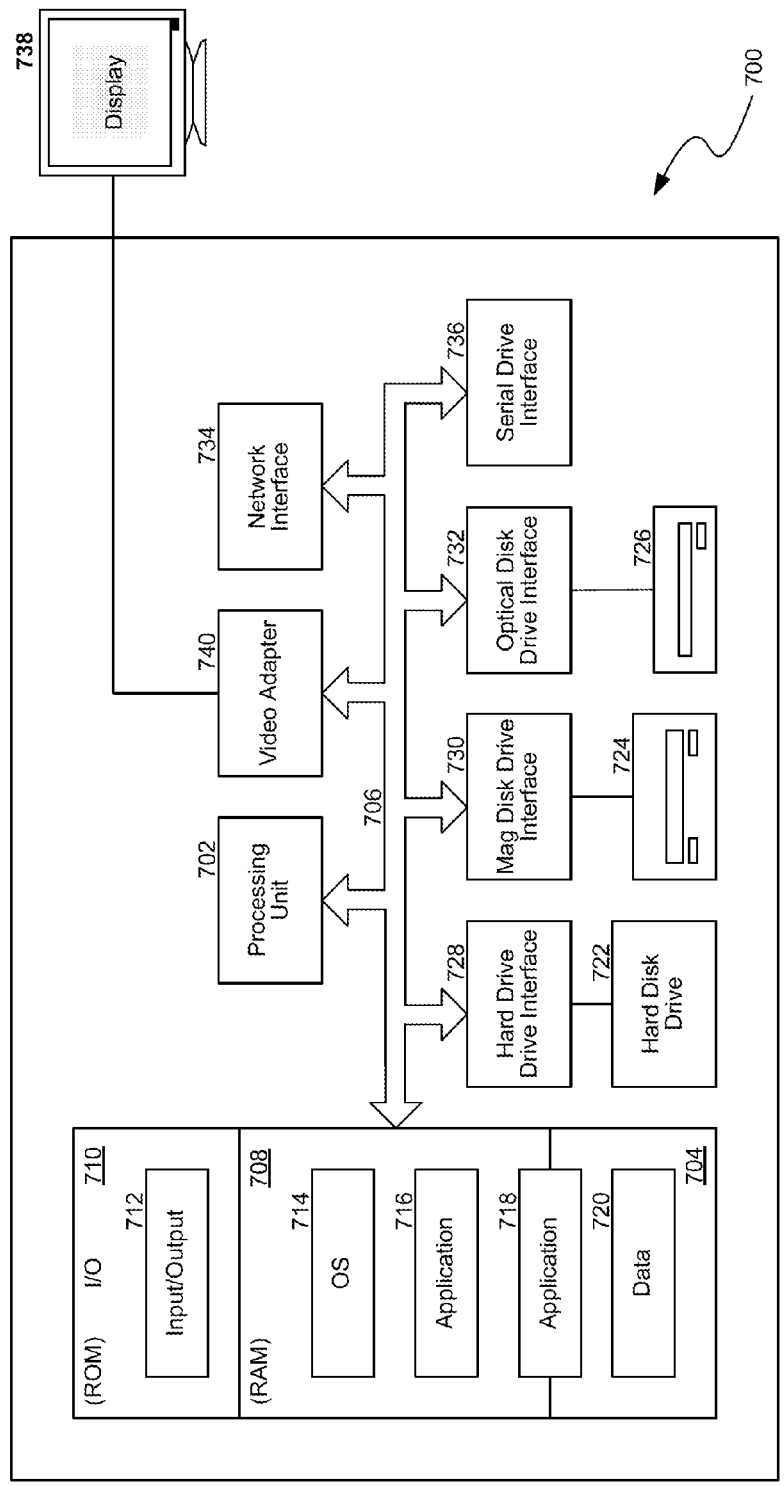
FIG. 7 depicts a functional block diagram of a device consistent with the technology of the present application.

Referring now to FIG. 7, a functional block diagram of a typical device 700 for the technology of the present application is provided. The device 700 is shown as a single, contained unit, such as, for example, a desktop, laptop, handheld, or mobile processor, but the device 700 may comprise portions that are remote and connectable via network connection such as via a LAN, a WAN, a WLAN, a WiFi Network, Internet, or the like. Generally, the device 700 includes a processor 702, a system memory 704, and a system bus 706. System bus 706 couples the various system components and allows data and control signals to be exchanged between the components. System bus 706 could operate on any number of conventional bus protocols. System memory 704 generally comprises both a random access memory (RAM) 708 and a read only memory (ROM) 710.

ROM 710 generally stores a basic operating information system such as a basic input/output system (BIOS) 712. RAM 708 often contains the basic operating system (OS) 714, application software 716 and 718, and data 720. System memory 704 contains the code for executing the functions and processing the data as described herein to allow the present technology of the present application to function as described. Client device 700 generally includes one or more of a hard disk drive 722 (which also includes flash drives, solid state drives, etc. as well as other volatile and non-volatile memory configurations), a magnetic disk drive 724, or an optical disk drive 726. The drives also may include zip drives and other portable devices with memory capability. The drives are connected to the bus 706 via a hard disk drive interface 728, a magnetic disk drive interface 730 and an optical disk drive interface 732, etc. Application modules and data may be stored on a disk, such as, for example, a hard disk installed in the hard disk drive (not shown). Client device 700 has network connection 734 to connect to a local area network (LAN), a wireless network, an Ethernet, the Internet, or the like, as well as one or more serial port interfaces 736 to connect to peripherals, such as a mouse, keyboard, modem, or printer. Client device 400 also may have USB ports or wireless components, not shown. Client device 700 typically has a display or monitor 738 connected to bus 706 through an appropriate interface, such as a video adapter 740. Monitor 738 may be used as an input mechanism using a touch screen, a light pen, or the like. On reading this disclosure, those of skill in the art will recognize that many of the components discussed as separate units may be combined into one unit and an individual unit may be split into several different units. Further, the various functions could be contained in one personal computer or spread over several networked personal computers. The identified components may be upgraded and replaced as associated technology improves and advances are made in computing technology. The speech recognition engines may have similar constructions.

The steps of a method or algorithm described in connection with the embodiments disclosed herein may be embodied directly in hardware, in a non-transient software module executed by a processor, or in a combination of the two. A non-transient software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal. For the purposes of the present application, the methods and computer program products described herein do not solely comprise electrical or carrier signals, and are non-transitory.

Although the technology has been described in language that is specific to certain structures, materials, and methodological steps, it is to be understood that the invention defined in the appended claims is not necessarily limited to the specific structures, materials, and/or steps described. Rather, the specific aspects and steps are described as forms of implementing the claimed invention. Since many embodiments of the invention can be practiced without departing from the spirit and scope of the invention, the invention resides in the claims hereinafter appended. Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

I claim:

1. A method performed on at least one processor for training a user audio profile without requiring a user to read known text, comprising the steps of:
    selecting a pre-recorded big audio file;
    automatically generating a plurality of little audio files from the pre-recorded big audio file;
    obtaining a big text file corresponding to the big audio file;
    generating a plurality of little text files using the big text file and endpointing metadata, wherein there is one little text file for each of the plurality of little audio files;
    creating a plurality of audio-text training pairs by linking each one of the plurality of little audio files with the corresponding one of the plurality of little text files;
    selecting at least one of the plurality of audio-text training pairs to train the user audio profile; and
    transmitting the at least one of the plurality of audio-text training pairs to a speech to text engine to train the user audio profile.

2. The method of claim 1 further comprising creating a user audio profile prior to transmitting the at least one of the plurality of audio-text training pairs, wherein the created user audio profile comprises a default profile.

3. The method of claim 1 further comprising:
    submitting the selected big audio file to the speech to text engine;
    creating the big text file from the big audio file and endpointing metadata; and
    splitting the big audio file into the plurality of little audio files using the endpointing metadata.

4. The method of claim 1 wherein the step of generating the plurality of little text files comprises using the big text file, a truth text file, and the endpointing metadata.

5. The method of claim 1 wherein the step of generating the plurality of little audio files from the big audio file comprises using an audiotimer to split the big audio file at predetermined intervals.

6. The method of claim 5 wherein the step of generating the plurality of little text files comprises creating a big truth text from the big audio file and splitting the big truth text at a predetermined word count.

7. The method of claim 1 wherein the plurality of audio-text pairs are linked at least by the endpointing metadata.

8. The method of claim 1 wherein the plurality of audio-text pairs are linked by at least one of tagging or indexing the plurality of little audio files and the plurality of little text files.

9. The method of claim 1 further comprising the step of displaying the plurality of audio-text pairs prior to transmitting the plurality of audio-text pairs to the speech to text engine for training.

10. The method of claim 9 further comprising editing the text of at least one of the plurality of audio-text pairs.

11. The method of claim 9 further comprising editing the audio of at least one of the plurality of audio-text pairs.

12. The method of claim 9 further comprising editing the text of at least one of the plurality of audio-text pairs and editing the audio of at least one of the plurality of audio-text pairs.

13. The method of claim 9 further comprising editing the text and the audio of at least one of the plurality of audio-text pairs.

14. An apparatus comprising:
    a processor, wherein the processor is operatively coupled to a speech to text engine;
    a memory operatively coupled to the processor; and
    a display operatively coupled to the processor and the memory;
        wherein the memory is configured to store audio and text files,
        wherein the processor is configured to fetch a big audio file from the memory and create a plurality of little audio files,
        wherein the processor is configured to obtain a big text file corresponding to the big audio file,
        wherein the processor is configured to generate a plurality of little text files using the big text file and endpointing metadata,
        wherein the processor is configured to link the plurality of little audio files and the plurality of little text files to create a plurality of audio-text training pairs that are displayed on the display, and
        wherein the processor is configured to transmit the plurality of audio-text training pairs to the speech to text engine for training a user audio profile.

15. The apparatus of claim 14 further comprising a text editor operatively coupled to the processor, wherein the text editor is configured to edit the text of the plurality of audio-text training pairs.

16. The apparatus of claim 14 further comprising an audio editor operatively coupled to the processor, wherein the audio editor is configured to edit the audio of the plurality of audio-text training pairs.

17. The apparatus of claim 14 further comprising a text editor and an audio editor operatively coupled to the processor, wherein the text editor is configured to edit the text of the plurality of audio-text training pairs and the audio editor is configured to edit the audio of the plurality of audio-text training pairs.

18. A non-transitory computer program product storable in a memory and executable by a computer comprising a computer usable medium including computer readable code embodied therein for processing data to allow training of a user audio profile, the computer usable medium comprising:
    code adapted to be executed by a processor configured to select a big audio file;

code adapted to be executed by a processor configured to generate a plurality of little audio files from the big audio file;

code adapted to be executed by a processor configured to obtain a big text file corresponding to the big audio file;

code adapted to be executed by a processor configured to generate a plurality of little text files using the big text file and endpointing metadata, wherein there is one little text file for each of the plurality of little audio files;

code adapted to be executed by a processor configured to create a plurality of audio-text training pairs by linking the plurality of little audio files with the corresponding plurality of little text files;

code adapted to be executed by a processor configured to display the plurality of audio-text training pairs;

code adapted to be executed by a processor configured to select at least one of the plurality of audio-text training pairs to train the user audio profile; and code adapted to be executed by a processor configured to transmit the at least one of the plurality of audio-text training pairs to a speech to text engine to train the user audio profile.

19. The computer program product of claim 18 comprising code adapted to be executed by a processor configured to edit at least the text of the audio-text training pairs displayed.

\* \* \* \* \*